United States Patent [19]

Galinsky

[11] 4,164,573

[45] Aug. 14, 1979

[54] COMPOSITION AND METHOD FOR MAKING A SUPPOSITORY FOR INTRODUCING A HYPOGLYCEMIC AGENT INTO A MAMMAL

[76] Inventor: Alvin M. Galinsky, 5518 Covode St., Pittsburgh, Pa. 15217

[21] Appl. No.: 586,638

[22] Filed: Jun. 13, 1975

[51] Int. Cl.$^2$ ............................................. A61K 37/26
[52] U.S. Cl. .................................................... 424/178
[58] Field of Search .......................................... 424/178

[56] References Cited

U.S. PATENT DOCUMENTS 2,373,625  4/1945  Brahn ................................... 424/178

*Primary Examiner*—Frederick E. Waddell
*Attorney, Agent, or Firm*—Buell, Blenko & Ziesenheim

[57] ABSTRACT

A method and composition for a rectally administered hypoglycemic agent into the bloodstream for the treatment of diabetes in mammals. The hypoglycemic agent is mixed with a physiological surface active agent which results in a suspension. This suspension is then mixed with a dispersion formed by dissolving MYRJ ™ 45, MYRJ ™ 51, ONESTA HARDENER ™ and COTMAR ™ in ether. This mixture is then evaporated and a semisolid mass results which is then shaped into a suppository.

9 Claims, No Drawings

COMPOSITION AND METHOD FOR MAKING A SUPPOSITORY FOR INTRODUCING A HYPOGLYCEMIC AGENT INTO A MAMMAL

I. THE PROBLEM PRESENTED TO THE INVENTOR

Since 1921 insulin has been the principal drug for the treatment of diabetes. There are certain disadvantages to the use of insulin. It can only be administered in a medically effective manner currently by a parenteral route; its use required periodic visits to a physician; the margin of safety in its use is narrow; and the parenteral administration is expensive and causes some discomfort. These problems stimulated the search for another route of administration which would give a comparable effect as that achieved by the parenteral administration. A considerable amount of research has been conducted to effect the administration of a hypoglycemic agent that is as effective as insulin administered parenterally but does not have its disadvantages. Such efforts, however, to date have been unsatisfactory.

Greater metabolic stability of insulin can be expected in the lower gastrointestinal tract because of the biological degradation of insulin by pepsin and trypsin in the upper gastrointestinal tract. This prompted the investigation and research for administering insulin into the lower gastrointestinal tract by utilizing the rectal route by a suppository vehicle containing the insulin.

THE PRIOR ART
II.

Prior to 1974, work on a suppository for the rectal administration of a hypoglycemic agent in mammals was completed at Duquesne University, Pittsburgh, Pennsylvania. The developed formulations have: (i) a suppository base consisting of COTMAR TM and ONESTA HARDENER TM; (ii) a synthetic surface active agent having polyoxyethylene stearates (or other synthetic surface active agent combinations of desired hydrophile-lipophile balance); and (iii) a hypoglycemic agent selected from the group consisting of soluble insulin, zinc insulin, protamine zinc insulin and globin insulin, with a preference for protamine zinc insulin.

However, the decrease in blood sugar obtained (with the composition optimally formulated) in mammalian test animals (rabbit) indicated that an inordinately large dose of protamine zinc insulin would be required in order to achieve a biological response equivalent to that obtainable by the parenteral route. Consequently, I sought to lessen this equibiological dosage gap. My invention incorporates the addition of physiological surface active agents into the previously developed formulation and it has enhanced the clinical efficacy of the suppository by a factor in excess of 100 percent.

III. DESCRIPTION OF THE INVENTION

I use a semisolid mixture having COTMAR TM and ONESTA HARDENER TM as a suppository base. This is combined with selected synthetic surface active agents; selected physiological surface active agents; and a hypoglycemic agent and fabricated into a rectal suppository by the solvent method of solid dispersion. The suppository vehicle is capable of carrying the hypoglycemic agent to the site of absorption into the bloodstream of mammals in clinically significant and reproducible concentrations following rectal administration.

Preferably, the mixture for the semisolid waxy type suppository base of COTMAR TM and ONESTA HARDENER TM is in a proportion of 16.7 parts COTMAR TM to 30.0 parts ONESTA HARDENER TM. This provides a combined base of suitable melting characteristics in vitro and in vivo when fabricated into a suppository along with the other constituents.

The synthetic surface active agent consists of polyoxyethylene stearates. Preferably used were MYRJ TM 45 and MYRJ TM 51. More preferably used was a mixture of MYRJ TM 45 and MYRJ TM 51 combined in such proportions to produce a hydrophile-lipophile balance of 12.73 on the Griffin HLB scale.

The physiological surface active agent was selected from a group consisting of cholic acid derivatives, deoxycholic acid derivatives, phospholipids and conjugated bile salts. Preferably the cholic acid derivatives are selected from the group consisting of salts of cholic acid, salts of glycocholic acid, salts of taurocholic acid and salts of glycotaurocholic acid. Preferably the deoxycholic acid derivatives are selected from the group consisting of salts of deoxycholic acid, salts of glycodeoxycholic acid, and salts of taurodeoxycholic acid. Preferably, the phospholipids are selected from the group consisting of synthetic lecithin and lysolecithin. More preferably, the phospholipids consist of synthetic lecithin in a 0.8 percent by weight concentration. Preferably, the conjugated bile salts are selected from the group consisting of glycodehydrocholic acid salts, taurodehydrocholic acid salts, glycolithocholic acid salts, taurolithocholic acid salts, glycochenodeoxycholic acid salts and taurochenodeoxycholic acid salts. More preferably the conjugated bile salt consists of sodium taurochenodeoxycholate in a 2.0 percent by weight concentration.

The hypoglycemic agent is selected from the group consisting of soluble insulin, zinc insulin, protamine zinc insulin and globin zinc insulin. Preferably, the hypoglycemic agent is protamine zinc insulin.

The method of manufacture of the suppository consists of a slight modification of the solid dispersion technique described by Chiou and Riegelman [J. Pharm. Sci., 58, 1505 (1969)]. The solvent employed to disperse the less soluble ingredients of the mixture into the suppository base was ether. In this manner, a more homogeneous dispersion of the hypoglycemic agent was obtained providing better clinical efficacy.

I provide a method of making a rectally administered suppository for the introduction of hypoglycemic agents into the rectum for absorption into the bloodstream for the treatment of diabetes in mammals comprising dissolving in ether at a temperature range between 25° C. and 45° C. MYRJ TM 45, MYRJ TM 51, ONESTA HARDENER TM and COTMAR TM which results in a dispersion; mixing a physiological surface active agent selected from the group consisting of cholic acid derivatives, deoxycholic acid derivatives, phospholipids and conjugated bile salts, with a hypoglycemic agent which results in a suspension; adding the dispersion to the suspension which provides a mixture; and evaporating the mixture by flash evaporation until all of the ether has evaporated which results in a semisolid mass that is then shaped into the suppository form.

IV. EXAMPLES

The invention can be understood also by reference to the following examples which illustrate both the preferred form of compositions and the methods of making them.

EXAMPLE 1

A composition was formulated according to the following formula:

| Protamine Zinc Insulin Suppository Formulation FORMULA I | |
|---|---|
| MYRJ ™ 45 (synthetic surface active agent) | 30.00% |
| MYRJ ™ 51 (synthetic surface active agent) | 15.00% |
| Synthetic Lecithin (physiological surface active agent [phospholipid]) | 0.80% |
| ONESTA HARDENER ™ (suppository base) | 30.00% |
| COTMAR ™ (suppository base) | 16.70% |
| Protamine Zinc Insulin Suspension (insulin 381 units/ml; protamine 1.25 mg/100 units) (hypoglycemic agent) | 7.50% |

1. Preparation Of Insulin Suppositories

The formulation was used to prepare an insulin suppository. The solvent method of solid dispersion was used. MYRJ ™ 45, MYRJ ™ 51, ONESTA HARDENER ™ and COTMAR ™ were dissolved in ether (75 ml) in a flask held under a flow of warm tap water. The synthetic lecithin dispersion was added to the insulin suspension in a round bottom flask and the cooled suppository base dispersion (MYRJ ™ 45, MYRJ ™ 51, ONESTA HARDENER ™, and COTMAR ™) was then added. The resultant liquid-liquid dispersion was flash evaporated. Final evaporation of the solvents was achieved via reduced pressure (0.5 mm Hg) evaporation. A minimum drying period of 30 minutes was employed. The suppository mass was weighed and distilled water was incorporated in sufficient volume to reconstitute the water content to formula strength. The suppositories were then shaped by hand. The weight of each suppository was approximately 0.350 g, accurately weighed. Blank suppositories were prepared by substituting water for the protamine zinc insulin in the formula. Control suppository formulations were prepared by substituting water for the physiological surface active agent in the formula.

2. Animal Selection And Preparation

The experimental animals were New Zealand, white, male young rabbits. Their weight ranged between 5.5 and 8.5 lbs. All rabbits utilized were fasted for a minimum period of 18 hours prior to their participation in any experiment.

3. Blood Sampling Technique

The rabbits were restrained in an animal restrainer. The restrainer facilitated the easy insertion of the suppository and convenient withdrawal of blood samples by positioning the rabbits in a comfortable manner with the experimental areas exposed. The area over the marginal vein of the ear of the rabbit was shaved and cleaned with alcohol. Xylene, a local irritant causing increased blood supply to the ear, was applied to the area when needed. A hemostat was then clamped lightly at the base of the ear, providing just sufficient pressure to occlude the vein. The swollen vein was then punctured with a needle attached to a syringe and the blood was allowed to pool on the ear. The blood was then drawn into the syringe which was previously rinsed with heparin solution (1000 units per ml) to prevent clotting in both the needle and the syringe. The blood was measured directly from the syringe by volume difference.

4. Analysis Of Blood Sugar Levels

One-tenth of a milliliter of blood sample was added to 1.9 ml of distilled water contained in each of two 15 ml centrifuge tubes. One milliliter of zinc sulfate solution and 1.0 ml of sodium hydroxide solution were added to each suspension. The contents were mixed and then centrifuged for 5 minutes at 1500 r.p.m. in order to separate the precipitated proteins. A 2.0 ml aliquot of the supernatant liquid was transferred to a clean test tube. the pH of the solution was determined, using pHydrion ™ paper which is a pH sensitive paper, and adjusted to 7.0 with sodium hydroxide or zinc sulfate.

A 0.1 ml aliquot of glucose reference standard (0.05% w/v) was treated with each reagent in the same order as the blood samples. This was used as a standard. Additionally, a 2.0 ml sample of distilled water was added to a test tube and treated with each reagent in the same manner as the blood and standard. The latter solution served as a blank, which corrected for any error that may have been introduced due to the enzyme itself, by the base solution and/or by the distilled water used.

Two milliliter aliquots of the enzyme solution were added to the series of blood samples as well as to the standard and the blank. The color of the solutions was allowed to develop for exactly 10.0 minutes. One drop of hydrochloric acid (4 N) was then added to stabilize the color. Absorbances at 425 nm were determined in a spectrophotometer. Blood sugar levels of the samples were then calculated from the formula:

$$C_u = A_u \times C_s / A_s$$

where:
A = absorbance
C = concentration in mg/100 ml
u = unknown
s = standard

5. Determination Of Rabbit Normal Blood Sugar Levels

Sixteen rabbits were deprived of solid food for a minimum of 18 hours before being employed in an experiment. The rabbits were divided into two equal groups. Blood samples were taken as described above. Each rabbit was then allowed to rest for a minimum of 48 hours and the blood sampling procedure was repeated until a total of ten blood samples were obtained from each of the rabbits. Mean blood sugar levels were determined mathematically for each animal.

6. Protocol Of Suppository Administration And Blood Sampling

Sixteen rabbits, divided into two groups, were used. A blank suppository was administered to one rabbit in each group which served as the control during each experiment. Blood samples were drawn before the suppository was administered and at intervals thereafter of 1.0 hr., 1.5 hrs., 2.5 hrs., 3.5 hrs., 4.5 hrs., and 5.5 hrs. A total of twenty determinations were conducted using each formulation. BSL (blood sugar level) minima were used exclusively to determine responses to formulation variables without regard to time considerations.

Control formulations containing protamine zinc insulin but no physiological surface active agent were used to calculate the percent enhancement of response due to the presence of physiological surface active agent.

7. Results And Evaluation

The effects on blood sugar level following administration of suppositories prepared using Formula I are depicted in Table I.

TABLE I
BLOOD SUGAR LEVEL DECREASE FOLLOWING RECTAL ADMINISTRATION OF PROTAMINE ZINC INSULIN SUPPOSITORY FORMULATION CONTAINING 0.8 PERCENT CONCENTRATION OF SYNTHETIC LECITHIN

| Animal | Blood Sugar Level Before Suppository (mg %) | Minimum Blood Sugar Level After Suppository (mg %) | Percent Decrease | Observed Time Of Maximum Blood Sugar Drop (hrs. ± 0.5) |
|---|---|---|---|---|
| 1C' | 86.54 | 84.62 | 2.22 | 1.5 |
| 2 | 84.50 | 20.00 | 76.33 | 1.5 |
| 3 | 84.62 | 41.35 | 51.13 | 1.5 |
| 4 | 85.58 | 25.96 | 69.66 | 1.5 |
| 5 | 85.58 | 36.54 | 57.30 | 1.5 |
| 6 | 83.65 | 30.77 | 62.02 | 1.0 |
| 7 | 80.77 | 50.00 | 38.08 | 1.5 |
| 8 | 87.50 | 37.50 | 57.14 | 1.5 |
| 9C' | 80.36 | 77.68 | 3.33 | 1.5 |
| 10 | 82.14 | 35.71 | 56.53 | 1.5 |
| 11 | 78.57 | 36.61 | 53.41 | 2.5 |
| 12 | 80.36 | 34.82 | 56.67 | 1.5 |
| 13 | 83.93 | 38.39 | 54.26 | 2.5 |
| 14 | 82.14 | 37.50 | 54.35 | 1.5 |
| 15 | 83.04 | 36.61 | 55.92 | 1.5 |
| 16 | 79.46 | 36.61 | 53.93 | 1.0 |
| 1 | 87.50 | 27.08 | 69.05 | 2.5 |
| 2C' | 79.17 | 75.00 | 5.27 | 1.5 |
| 3 | 80.21 | 35.42 | 55.85 | 2.5 |
| 4 | 82.29 | 21.88 | 73.42 | 1.0 |
| 5 | 78.13 | 33.33 | 57.34 | 1.5 |
| 6 | 84.38 | 39.58 | 53.09 | 1.0 |
| 7 | 86.46 | 38.54 | 55.42 | 1.5 |
| 8 | 84.38 | 35.42 | 58.03 | 1.5 |
| 9 | 88.00 | 22.00 | 75.00 | 1.5 |
| 10C' | 76.67 | 72.50 | 5.44 | 1.5 |
| 11 | 77.50 | 30.83 | 60.22 | 2.5 |
| 12 | 80.00 | 27.50 | 65.63 | 1.0 |
| 13 | 78.33 | 35.83 | 54.25 | 1.0 |
| 14 | 78.33 | 32.50 | 58.51 | 1.5 |
| 15 | 77.50 | 36.67 | 52.69 | 1.5 |
| 16 | 79.17 | 30.83 | 61.05 | 1.5 |
| Mean | 82.29 | 33.78 | 58.80 | |
| S.D. | 3.29 | 6.45 | 8.14 | t = 35.45 |
| S.E. | 0.62 | 1.22 | 1.54 | p < 0.05 |

C' indicates control values and are not included in the calculation of means, standard deviations, or standard errors.

These results were statistically evaluated according to the formulae:

$$\text{Standard Deviation } (S.D.) = \sqrt{\frac{\epsilon d^2}{n-1}} \quad \text{(Eq. 1)}$$

$$\text{Standard Error } (S.E.) = \frac{S.D.}{\sqrt{n}} \quad \text{(Eq. 2)}$$

$$\text{Student 't' Test (unpaired observations and equal size samples)} = \frac{\text{Mean}_1 - \text{Mean}_2}{\sqrt{(S.E._1)^2 + (S.E._2)^2}} \quad \text{(Eq. 3)}$$

where:
$d$ = deviation from the mean value
$n$ = number of test subjects

A cumulative comparison was made of the percent enhancement of the desired effect that was brought about by the formula suppository following exact duplication of the experimental procedures here described substituting other concentrations of synthetic lecithin or other physiological surface active agents selected from the group consisting of cholic acid derivatives, deoxycholic acid derivatives and phospholipids in varying concentrations. The results of such comparison are included in Table II.

TABLE II
CUMULATIVE COMPARISON OF THE PECENT ENHANCEMENT OF BLOOD SUGAR LEVEL DECREASE OF PROTAMINE ZINC INSULIN PRODUCED BY PHYSIOLOGIC SURFACTANTS

| Physiologic Surfactant Used | Percent Conc. | Average[a] Percent Decrease In Blood Sugar Level (mean ± S.E.) | Percent[b] Enhancement |
|---|---|---|---|
| Synthetic Lecithin | 0.8 | 58.80 ± 1.54 | 123.83 |
| Sodium Taurodeoxycholate | 2.0 | 65.97 ± 0.81 | 113.56 |
| Sodium Taurodeoxycholate | 1.0 | 62.62 ± 1.13 | 102.72 |
| Synthetic Lecithin | 0.6 | 53.15 ± 0.97 | 102.30 |
| Sodium Glycodeoxycholate | 2.0 | 61.45 ± 1.14 | 98.93 |
| Sodium Glycodeoxycholate | 1.0 | 60.15 ± 1.31 | 94.72 |
| Synthetic Lecithin | 0.4 | 50.74 ± 1.05 | 93.15 |
| Sodium Deoxycholate | 2.0 | 58.38 ± 1.34 | 88.99 |
| Synthetic Lecithin | 0.2 | 48.25 ± 1.05 | 83.67 |
| Sodium Deoxycholate | 1.0 | 50.33 ± 0.90 | 62.93 |
| Sodium Glycotaurocholate | 2.0 | 70.35 ± 1.28 | 47.72 |
| Sodium Glycocholate | 2.0 | 69.96 ± 1.31 | 46.61 |
| Sodium Taurocholate | 2.0 | 67.41 ± 1.23 | 41.26 |
| Sodium Glycotaurocholate | 1.0 | 66.20 ± 1.66 | 38.73 |
| Sodium Glycocholate | 1.0 | 62.56 ± 1.10 | 31.10 |
| Sodium Taurocholate | 1.0 | 62.35 ± 1.01 | 30.66 |
| Sodium Cholate | 2.0 | 62.35 ± 0.56 | 30.66 |
| Sodium Cholate | 1.0 | 59.33 ± 0.89 | 24.33 |
| Lysolecithin | 0.6 | 30.41 ± 1.24 | 15.76 |

TABLE II-continued
CUMULATIVE COMPARISON OF THE PECENT ENHANCEMENT OF BLOOD SUGAR LEVEL DECREASE OF PROTAMINE ZINC INSULIN PRODUCED BY PHYSIOLOGIC SURFACTANTS

| Physiologic Surfactant Used | Percent Conc. | Average[a] Percent Decrease In Blood Sugar Level (mean ± S.E.) | Percent[b] Enhancement |
|---|---|---|---|
| Lysolecithin | 0.4 | 27.98 ± 1.05 | 6.51 |

[a]values have been calculated by using the formula $(m - m_o) \times 100/m_o$, where, m = the blood sugar level before suppository (mg%) and $m_o$ = minimum blood sugar level after suppository (mg%).
[b]values have been calculated by using the formula $(m_1 - m_2) \times 100 m_2$, where, $m_1$ = the average percent decrease in blood sugar level obtained for the respective physiologic surfactant and $m_2$ = average percent decrease in blood sugar level obtained for the respective control formulation.

EXAMPLE 2

The formula used for the composition was as follows:

Protamine Zinc Insulin Suppository Formulation
FORMULA II

| | (% w/w) |
|---|---|
| MYRJ ™ 45 (synthetic surface active agent) | 30.00 |
| MYRJ ™ 51 (synthetic surface active agent) | 15.00 |
| ONESTA HARDENER ™ (suppository base) | 30.00 |
| COTMAR ™ (suppository base) | 16.70 |
| Sodium Taurochenodeoxycholate (physiological surface active agent [conjugated bile salt]) | 2.00 |
| Protamine Zinc Insulin Suspension (insulin, 454 units/ml; protamine, 1.25 mg/100 units) (hypoglycemic agent) | 6.30 |

1. Preparation Of Insulin Suppositories
   This was the same as Example 1.
2. Animal Selection And Preparation
   This was the same as Example 1.
3. Blood Sampling Technique
   This was the same as Example 1.
4. Analysis Of Blood Sugar Levels
   This was the same as Example 1.
5. Determination Of Rabbit Normal Blood Sugar Levels (Control)
   This was the same as Example 1 except twelve rabbits were used.
6. Protocol Of Suppository Administration And Blood Sampling
   This was the same as Example 1 except twelve rabbits were used.
7. Results And Evaluation Table III replaces Table I in Example 1 and Table II in Example 1 is replaced by the following:

The effectiveness of the conjugated bile salts employed in this study did vary in their ability to increase the desired biological response. Arranged in descending order of effectiveness, they are:
   a. Sodium Taurochenodeoxycholate
   b. Sodium Taurodehydrocholate
   c. Sodium Glycolithocholate
   d. Sodium Glycodehydrocholate
   e. Sodium Glycochenodeoxycholate
   f. Sodium Taurolithocholate As a result of the optimal formulation found in this study (Formula II), a rectal suppository dose of 11.8 units of insulin was found to be biologically equivalent to 0.6 units of insulin administered subcutaneously (the preferred parenteral route).

TABLE III
BLOOD SUGAR LEVEL DECREASE FOLLOWING RECTAL ADMINISTRATION OF PROTAMINE ZINC INSULIN SUPPOSITORY FORMULATION CONTAINING 2.0 PERCENT CONCENTRATION OF SODIUM TAUROCHENODEOXYCHOLATE

| Animal | BSL Before Suppository (mg %) | Minimum BSL After Suppository (mg %) | Percent Decrease in BSL | Percent Enhancement Of Response | Observed Time Of Maximum BSL Drop (hrs. ± 0.5) |
|---|---|---|---|---|---|
| 1 | 73.96 | 27.08 | 63.39 | 154.68 | 2.5 |
| 2 | 75.00 | 32.29 | 56.95 | 128.81 | 1.5 |
| 3 | 72.92 | 27.08 | 62.86 | 152.55 | 2.5 |
| 4C' | 71.88 | 69.79 | 2.91 | | 1.5 |
| 5 | 80.21 | 30.21 | 62.34 | 150.46 | 2.5 |
| 6 | 77.08 | 29.17 | 62.16 | 149.74 | 2.5 |
| 7 | 82.00 | 38.00 | 53.66 | 115.59 | 1.5 |
| 8 | 85.00 | 35.00 | 58.82 | 136.32 | 2.5 |
| 9C' | 77.00 | 73.00 | 5.19 | | 1.0 |
| 10 | 79.00 | 29.00 | 63.29 | 154.28 | 2.5 |
| 11 | 82.00 | 33.00 | 59.76 | 140.10 | 1.5 |
| 12 | 84.00 | 32.00 | 61.90 | 148.69 | 2.5 |
| 1 | 75.51 | 28.57 | 62.16 | 149.74 | 2.5 |
| 2 | 79.59 | 32.65 | 58.98 | 136.96 | 2.5 |
| 3C' | 74.49 | 71.43 | 4.11 | | 1.5 |
| 4 | 73.47 | 30.61 | 58.34 | 134.39 | 1.5 |
| 5 | 83.67 | 27.55 | 67.07 | 169.47 | 2.5 |
| 6 | 79.59 | 30.61 | 61.54 | 147.25 | 2.5 |
| 7 | 81.63 | 34.69 | 57.50 | 131.02 | 1.5 |
| 8 | 83.67 | 32.65 | 60.98 | 145.00 | 2.5 |
| 9 | 79.59 | 33.67 | 57.70 | 131.82 | 1.5 |
| 10C' | 80.61 | 77.55 | 3.80 | | 1.0 |
| 11 | 83.67 | 34.69 | 58.54 | 135.19 | 1.5 |
| 12 | 84.69 | 31.63 | 62.65 | 151.71 | 2.5 |
| Mean | 79.81 | 31.51 | 60.53 | 143.19 | |
| S.D. | 3.96 | 2.93 | 3.01 | 12.09 | t = 3.39 |
| D.E. | 0.89 | 0.66 | 0.67 | 2.70 | p < 0.05 |

C' indicates control values and are not included in the calculation of mean, standard deviation, or standard errors.

V. DEFINITIONS

1. MYRJ ™ 45: A synthetic surface active agent produced commercially by ICI United States Incorporated, Wilmington, Delaware, and known generically as polyoxyethylene-8-stearate.
2. MYRJ ™ 51: A synthetic surface active agent produced commercially by ICI United States Incorporated, Wilmington, Delaware and known generically as polyoxyethylene-30-stearate.
3. COTMAR ™: A semisolid, wax-like substance produced by Proctor & Gamble Company, Cincinnati, Ohio, consisting of partially hydrogenated cottonseed oil. (available approximately 1972)

4. ONESTA HARDENER TM: A semisolid, wax-like substance produced by Proctor & Gamble Company, Cincinnati, Ohio, consisting of completely hydrogenated peanut oil. (available approximately 1972)

I claim:

1. An article of manufacture for the introduction of hypoglycemic agents into the bloodstream for the treatment of diabetes in mammals by a rectally administered suppository comprising:
   (a) a suppository base consisting of a wax-like substance of partially hydrogenated cottonseed oil 16.7 percent by weight of the suppository and completely hydrogenated peanut oil 30.0 percent by weight of the suppository;
   (b) a synthetic surface active agent having polyoxyethylene stearates with a hydrophile-lipophile balance of 12.73 on the Griffin HLB scale;
   (c) a physiological surface active agent 0.8 percent by weight of the suppository selected from the group consisting of salts of cholic acid, salts of glycocholic acid, salts of taurocholic acid, salts of glycotaurocholic acid, salts of deoxycholic acid, salts of glycodeoxycholic acid, salts of taurodeoxycholic acid, salts of glycodehydrocholic acid, salts of taurodehydrocholic acid, salts of glycolithocholic acid, salts of taurolithocholic acid, salts of glycochenodeoxycholic acid, salts of taurochenodeoxycholic acid, synthetic lecithin and lysolecithin; and
   (d) insulin which is 7.5 percent by weight of the suppository.

2. An article of manufacture as recited in claim 1 wherein the polyoxyethylene stearates are polyoxyethylene-8-stearate and polyoxyethylene-30-stearate.

3. An article of manufacture for the introduction of hypoglycemic agents into the bloodstream for the treatment of diabetes in mammals by a rectally administered suppository comprising:
   (a) a suppository base consisting of a wax-like substance of partially hydrogenated cottonseed oil 16.7 percent by weight of the suppository and completely hydrogenated peanut oil 30.0 percent by weight of the suppository;
   (b) a synthetic surface active agent having polyoxyethylene stearates with a hydrophile-lipophile balance of 12.73 on the Griffin HLB scale;
   (c) a physiological surface active agent 2.0 percent by weight of the suppository selected from the group consisting of salts of cholic acid, salts of glycocholic acid, salts of taurocholic acid, salts of glycotaurocholic acid, salts of deoxycholic acid, salts of glycodeoxycholic acid, salts of taurodeoxycholic acid, salts of glycodehydrocholic acid, salts of taurodehydrocholic acid, salts of glycolithocholic acid, salts of taurolithocholic acid, salts of glycochenodeoxycholic acid, salts of taurochenodeoxycholic acid, synthetic lecithin and lysolecithin; and
   (d) insulin which is 6.30 percent by weight of the suppository.

4. An article of manufacture as recited in claim 3 wherein the polyoxyethylene stearates are polyoxyethylene-8-stearate and polyoxyethylene-30-stearate.

5. An article of manufacture for the introduction of hypoglycemic agents into the bloodstream for the treatment of diabetes in mammals by a rectally administered suppository comprising:
   (a) a suppository base consisting of a wax-like substance of partially hydrogenated cottonseed oil and completely hydrogenated peanut oil;
   (b) a synthetic surface active agent having polyoxyethylene stearates;
   (c) a physiological surface active agent present in an amount effective to enhance a decrease in blood sugar levels and selected from the group consisting of salts of cholic acid, salts of glycocholic acid, salts of taurocholic acid, salts of glycotaurocholic acid, salts of deoxycholic acid, salts of glycodeoxycholic acid, salts of taurodeoxycholic acid, salts of glycodehydrocholic acid, salts of taurodehydrocholic acid, salts of glycolithocholic acid, salts of taurolithocholic acid, salts of glycochenodeoxycholic acid, salts of taurochenodeoxycholic acid, synthetic lecithin and lysolecithin; and
   (d) insulin.

6. An article of manufacture as recited in claim 5 wherein the polyoxyethylene stearates are polyoxyethylene-8-stearate and polyoxyethylene-30-stearate.

7. A method of making a rectally administered suppository for the introduction of hypoglycemic agents into the bloodstream for the treatment of diabetes in mammals comprising:
   (a) dissolving in ether at a temperature range between 25° C. and 45° C. polyoxyethylene-8-stearate and polyoxyethylene-30-stearate having a hydrophile-lipophile balance of 12.73 on the Griffin HLB scale and a semisolid wax-like substance consisting of partially hydrogenated cottonseed oil 16.7 percent by weight of the suppository and completely hydrogenated peanut oil 30.0 percent by weight of the suppository which results in a dispersion;
   (b) mixing a physiological surface active agent 0.8 percent by weight of the suppository selected from the group consisting of salts of cholic acid, salts of glycocholic acid, salts of taurocholic acid, salts of glycotaurocholic acid, salts of deoxycholic acid, salts of glycodeoxycholic acid, salts of taurodeoxycholic acid, salts of glycodehydrocholic acid, salts of taurodehydrocholic acid, salts of glycolithocholic acid, salts of taurolithocholic acid, salts of glycochenodeoxycholic acid, salts of taurochenodeoxycholic acid, synthetic lecithin and lysolecithin, with insulin of 7.5 percent by weight of the suppository which results in a suspension;
   (c) adding the dispersion to the suspension which provides a mixture; and
   (d) evaporating the mixture by flash evaporation until all of the ether has evaporated which results in a semisolid mass that is then shaped into the suppository form.

8. A method of making a rectally administered suppository for the introduction of hypoglycemic agents into the bloodstream for the treatment of diabetes in mammals comprising:
   (a) dissolving in ether at a temperature range between 25° C. and 45° C. polyoxyethylene-8-stearate and polyoxyethylene-30-stearate having a hydrophile-lipophile balance of 12.73 on the Griffin HLB scale and a semisolid wax-like substance consisting of partially hydrogenated cottonseed oil 16.7 percent by weight of the suppository and completely hydrogenated peanut oil 30.0 percent by weight of the suppository which results in a dispersion;

(b) mixing a physiological surface active agent 2.0 percent by weight of the suppository selected from the group consisting of salts of cholic acid, salts of glycocholic acid, salts of taurocholic acid, salts of glycotaurocholic acid, salts of deoxycholic acid, salts of glycodeoxycholic acid, salts of taurodeoxycholic acid, salts of glycodehydrocholic, salts of taurodehydrocholic acid, salts of glycolithocholic acid, salts of taurolithocholic acid, salts of glycochenodeoxycholic acid, salts of taurochenodeoxycholic acid, synthetic lecithin and lysolecithin with insulin of 6.3 percent by weight of the suppository which results in a suspension;

(c) adding the dispersion to the suspension which provides a mixture; and (d) evaporating the mixture by flash evaporation until all of the ether has evaporated which results in a semisolid mass that is then shaped into the suppository form.

9. A method of making a rectally administered suppository for the introduction of hypoglycemic agents into the bloodstream for the treatment of diabetes in mammals comprising:

(a) dissolving in ether at a temperature range between 25° C. and 45° C. polyoxyethylene-8-stearate and polyoxyethylene-30-stearate and a semisolid wax-like substance consisting of partially hydrogenated cottonseed oil and completely hydrogenated peanut oil which results in a dispersion;

(b) mixing a physiological surface active agent present in an amount effective to enhance a decrease in blood sugar levels and selected from the group consisting of salts of cholic acid, salts of salts of glycocholic acid, salts of taurocholic acid, salts of glycocholic acid, salts of deoxycholic acid, salts of glycodeoxycholic acid, salts of taurodeoxycholic acid, salts of glycodehydrocholic acid, salts of taurodehydrocholic acid, salts of glycolithocholic acid, salts of taurolithocholic acid, salts of glycochenodeoxycholic acid, salts of taurochenodeoxycholic acid, synthetic lecithin and lysolecithin with insulin which results in a suspension;

(c) adding the dispersion to the suspension which provides a mixture; and (d) evaporating the mixture by flash evaporation until all of the ether has evaporated which results in a semisolid mass that is then shaped into the suppository form.

* * * * *

UNITED STATES PATENT AND TRADEMARK OFFICE
CERTIFICATE OF CORRECTION

PATENT NO. : 4,164,573

DATED : September 12, 1979

INVENTOR(S) : Alvin M. Galinsky

It is certified that error appears in the above-identified patent and that said Letters Patent are hereby corrected as shown below:

Column 6, under TABLE II, in the second line of the heading, "PECENT" should read --PERCENT--.

Column 7, under TABLE II-continued, in the second line of the heading, "PECENT" should read --PERCENT--.

Column 8, in the last line of TABLE III, under the "Animal" column, "D.E." should be --S.E.--.

Claim 9, column 12, line 8, "salts of" (third occurrence) should be deleted.

Claim 9, column 12, line 10, "glycocholic" should be deleted and should read --glycotaurocholic--.

Signed and Sealed this

Thirteenth Day of November 1979

[SEAL]

Attest:

RUTH C. MASON
Attesting Officer

LUTRELLE F. PARKER
Acting Commissioner of Patents and Trademarks